United States Patent
MacKay

(10) Patent No.: US 8,852,639 B2
(45) Date of Patent: Oct. 7, 2014

(54) ANTIMICROBIAL FOAM AND METHOD OF MANUFACTURE

(75) Inventor: Walter MacKay, Bloomburg, PA (US)

(73) Assignee: Crest Foam Industries, Moonachie, NJ (US)

(*) Notice: Subject to any disclaimer, the term of this patent is extended or adjusted under 35 U.S.C. 154(b) by 561 days.

(21) Appl. No.: 12/707,742

(22) Filed: Feb. 18, 2010

(65) Prior Publication Data

US 2011/0200674 A1 Aug. 18, 2011

(51) Int. Cl.
*A61K 9/14* (2006.01)
*A61K 33/38* (2006.01)

(52) U.S. Cl.
CPC ................................ *A61K 33/38* (2013.01)
USPC ............................ 424/486; 424/618

(58) Field of Classification Search
None
See application file for complete search history.

(56) References Cited

U.S. PATENT DOCUMENTS

| 4,231,901 A | 11/1980 | Berbeco |
| 4,664,662 A | 5/1987 | Webster |
| 4,937,273 A | 6/1990 | Okuyama et al. |
| 5,409,472 A | 4/1995 | Rawlings et al. |
| 5,489,617 A | 2/1996 | Miller et al. |
| 5,971,531 A * | 10/1999 | Dietl et al. ........................ 347/86 |
| 6,371,606 B1 * | 4/2002 | Free ............................... 347/86 |
| 6,706,773 B1 | 3/2004 | McGoff et al. |
| 6,977,323 B1 | 12/2005 | Swenson |
| 7,078,060 B2 | 7/2006 | Burrell et al. |
| 7,118,761 B2 | 10/2006 | Canada et al. |
| 7,232,210 B2 * | 6/2007 | Cho et al. ........................ 347/86 |
| 7,314,840 B2 | 1/2008 | Baychar |
| 7,470,437 B2 | 12/2008 | Burrell et al. |
| 2005/0211635 A1 | 9/2005 | Yeh et al. |
| 2007/0003603 A1 * | 1/2007 | Karandikar et al. .......... 424/443 |

FOREIGN PATENT DOCUMENTS

| JP | 02269141 A | 11/1990 |
| JP | 2004-256794 | 9/2004 |
| WO | 0134686 A1 | 5/2001 |
| WO | WO 2006/001182 | 1/2006 |
| WO | WO 2006/038761 | 4/2006 |
| WO | WO 2008/104276 | 9/2008 |

OTHER PUBLICATIONS

International Search Report for PCT/US2011/024687, mailed Apr. 19, 2011.

* cited by examiner

*Primary Examiner* — Brian Gulledge
(74) *Attorney, Agent, or Firm* — Thomas, Karceski & Karmilovich, PC

(57) ABSTRACT

An antimicrobial foam includes an open-cell foam in a foam matrix defining a plurality of interconnected bubbles therein. Silver nanoparticles are suspended within the foam matrix. The foam matrix may be made from polyether polyurethane, polyester polyurethane, polycarbonate, thermoplastic olefin, thermoplastic elastomer, and thermoplastic polyurethane. The silver nanoparticles may have an average size between about 5 and 100 nanometers. The silver nanoparticles may be incorporated into the foam matrix in a concentration of between about 0.01 weight-% and about 0.20 weight-%. A method of manufacture of the foam also is described.

17 Claims, 5 Drawing Sheets

Dry Environment

ANTIMICROBIAL FOAM AND METHOD OF MANUFACTURE

CROSS-REFERENCE TO RELATED APPLICATION(S)

This is a Non-Provisional United States patent application that does not rely for priority on any prior-filed patent application.

FIELD OF THE INVENTION

The present invention concerns foam with enhanced antimicrobial characteristics and a method of manufacturing the same. In one contemplated embodiment, the present invention concerns a reticulated (open-cell) foam incorporating nanoparticles of silver as an anti-microbial agent and a method of manufacturing the anti-microbial foam containing the silver nanoparticles.

DESCRIPTION OF RELATED ART

Among the elements in the periodic table, silver has been known as an antibacterial agent for many hundreds of years. For example, Egyptians used silver in drinking water, Roman soldiers used silver for wound healing, and the Chinese used silver for eating utensils.

Silver is recognized as an elemental material that presents low toxicity toward humans and animals. However, silver presents a significant toxicity to over six hundred species of bacteria, fungi, and viruses, making silver an excellent choice as an antibacterial, antifungal, antiviral agent and/or antimicrobial.

For example, U.S. Pat. No. 4,664,662 (hereinafter "the '662 patent) describes an absorbent, non-adherent wound dressing that includes an absorbent material in the form of a conformable, resilient, absorbent, hydrophilic foam retained within a porous bag formed from a polymeric bag formed from a perforated polymeric film. (See the '662 patent at the Abstract.) The foam may be a resilient, open cell foam. (The '662 patent at col. 3, line 9.) The foam may be made from polyurethane, carboxylated butadiene-styrene rubber, polyacrylate, polyvinylic, or cellulosic foams. (The '662 patent at col. 3, lines 26-28.) Favored foams include crosslinked hydrophilic polyurethane. (The '662 patent at col. 3, lines 48-49.) The polyurethane foam may be a polyester or polyester polyurethane foam. (The '662 patent at col. 5, lines 16-18.) The wound dressing may be treated with antibacterial agents including a silver salt such as silver sulphadiazine. (The '662 patent at col. 8, lines 2-7.) The antibacterial agent may be incorporated into the foam during the process of manufacturing the foam or just prior to use by soaking the foam in a solution of the components. (The '662 patent at col. 8, lines 8-13.)

U.S. Pat. No. 4,937,273 (hereinafter "the '273 patent") describes a process for producing antibacterial flexible polyurethane foam. The background section of the patent describes how flexible polyurethane foams have been used as kitchen cleaners, body sponges, puffs, filter elements, and mattresses. (The '273 patent at col. 1, lines 11-13.) The background section also describes that these articles have been known to be impregnated with antibacterial agents. (The '273 patent at col. 1, lines 13-19.) According to the '273 patent, a problem with this existing approach is that the antibacterial foam does not retain its antibacterial action for an extended period of time, because the antibacterial agent soon escapes from the open cells. (The '273 patent at col. 1, lines 19-22.) To resolve this problem, the '273 patent describes a flexible polyurethane foam where the antibacterial agent is incorporated into the foam in the form of silver, copper, or zinc ions supported on zeolite. (The '273 patent at col. 1, lines 34-46.) The antibacterial agent may be a powder with an average particle diameter of 0.1 to 1 µm. (The '273 patent at col. 4, lines 9-11.) A preferred amount of the antibacterial agent may be more than 0.1 parts be weight, or 0.1 to 3 parts by weight for 100 parts of polyol. (The '273 patent at col. 4, lines 14-16.)

U.S. Pat. No. 6,706,773 (hereinafter "the '773 patent") describes a process for preparing a foam component. The foam component may incorporate active ingredients including antibacterial agents. (The '773 patent at col. 13, lines 55-64.) A foam stabilizer also may be added in the form of silver sulphate, carbonate, oxide, chloride, bromide, iodide, phosphate, borate, acetate, citrate, and nitrate. (The '773 patent at col. 15, lines 41-48.) The stabilizers may be added as finely divided particles having an average particle size of less than 10 micrometers, preferably less than 1 micrometer, 0.5 micrometers, or 0.1 micrometers. (The '773 patent at col. 15, lines 49-55.)

U.S. Pat. No. 6,977,323 (hereinafter "the '323 patent") describes a foam-on-film medical article that combines a polyurethane foam and a moisture-permeable, polymeric film. (The '323 patent at col. 1, lines 55-66.) A topically active medicament, such as an antibacterial agent (i.e., a silver salt) may be present in the foam layer. (The '323 patent at col. 5, lines 57-67.)

U.S. Pat. No. 7,118,761 (hereinafter "the '761 patent") describes a method for producing a silver-containing wound care device. The substrates for the wound care device for receiving the silver-based antimicrobial finish include fibers, fabrics, foams, alginates, hydrogels, and hydrocolloids. (The '761 patent at col. 4, lines 61-64.) Foams generally refer to cellular polymeric structure, and preferably an open cell structure. (The '761 patent at col. 5, lines 53-54.) Suitable foams include synthetic organic polymers as polyurethane, carboxylated butadiene styrene rubber, polyester, and polyacrylate. (The '761 patent at col. 5, lines 54-56.) A silver ion-containing compound, such as silver sodium hydrogen zirconium phosphate, is included in a binder that is coated onto the substrate. (The '761 patent at col. 8, lines 29-30 and lines 56-65.) The binders may include polyurethane and acrylic binders. (The '761 patent at col. 9, lines 51-55.)

U.S. Pat. No. 7,232,210 (hereinafter the '210 patent") describes a foam for ink printer cartridges that contain 0.1-5.0 wt % of silver nanoparticles based on the total weight of the foam. (The '210 patent at the Abstract.) The foam may be one of polyester resin, polyurethane resin, isocyanate resin, polysiloxane resin, and a mixture thereof. (The '210 patent at col. 3, lines 5-10.) The silver nanoparticles are contained in the foam in an amount of 0.1-5.0 wt % based on the weight of the foam. (The '210 patent at col. 2, lines 57-59.) Less than 0.1 wt % of silver fails to provide sufficient antibacterial properties while silver in excess of 5.0 wt % does not increase the antibacterial properties of the foam and becomes economically unfeasible. (The '210 patent at col. 2, lines 59-63.) The silver nanoparticles have sizes from 30 nm to 100 µm. (The '210 patent at col. 2, lines 64-66.) If the nanoparticles are less than 30 nm in size, they become difficult to manufacture. On the other hand, when the silver nanoparticles exceed 100 µm in size, they are not uniformly dispersed in the foam. (The '210 patent at col. 2, line 66, through col. 3, line 3.)

U.S. Pat. No. 7,314,840 (hereinafter "the '840 patent") describes a liner for boots that may include an open cell hydrophilic foam that includes anti-microbial silver fibers. (The '840 patent at col. 8, lines 31-36.)

U.S. Pat. No. 7,470,437 (hereinafter "the '437 patent") describes methods of treating conditions with metal-containing materials. In this patent, a metal-containing compound may be incorporated into a pharmaceutically-acceptable carrier such as a foam. (The '437 patent at col. 3, lines 1-8.) The metal may include antimicrobial, atomically disordered, nanocrystalline silver-containing materials. (The '437 patent at col. 3, lines 50-60.) As discussed in the reference, a nanocrystalline material is a single-phase polycrystal or multiphase polycrystal having a maximum dimension of about 100 nanometers or less. (The '437 patent at col. 6, lines 12-19.) The nanocrystalline materials may be deposited as a coating on a surface of a substrate. (The '437 patent at col. 13, lines 37-46.) Alternatively, the nanocrystalline materials may be incorporated into a topically-applied pharmaceutical carrier such as a cream, ointment, gel, lotion, paste, foam, and liposome. (The '437 patent at col. 19, lines 25-27.)

PCT Patent Application Publication No. WO 2008/104276 describes a silver-containing foam structure. According to the abstract, the invention is directed to a hydrophilic polyurethane foam structure that contains a silver salt chosen from the group of silver sulphate, silver citrate, silver acetate, silver carbonate, silver lactate, and silver phosphate mixed into the foam.

PCT Patent Application Publication No. WO 2006/038761 (hereinafter "the '761 Application") describes an antibacterial latex foam containing nano-silver particles, where the latex foam may be used to manufacture mattresses for health care use. (The '761 Application at paragraph [4].) Silver powder may be incorporated into the latex foam in an amount of 0.005 to 0.1 weight parts based on 100 weight parts of rubber latex. (The '761 Application at paragraph [58].) The silver particles may have a size from 1 to 100 nanometers. (The '761 Application at paragraph [59].) According to the '761 Application, if the silver content is less than 0.005 weight %, the latex foam loses its antibacterial properties. However, when the silver content exceeds 0.1 weight %, antibacterial properties are not improved and the silver can react with sulfur to create unattractive black spots on the foam. (The '761 Application at paragraph [60].)

As far as the English Abstract provides, PCT Patent Application Publication No. WO 2006/00182 is directed to a foamed article that contains fibers having surfaces coated with silver and silver oxide to provide antibacterial properties to the foam.

According to the English abstract, Japanese Patent Application No. JP 2004-256794 describes a polyurethane foam that contains an antibacterial agent such as silver and titanium dioxide and a carbon powder.

One problem associated with the prior art lies in the duration of the efficacy of silver when applied as a coating to open or closed cell foams.

When silver is applied in a coating to a substrate, the silver has a tendency to wash off of the underlying substrate over a period of time.

SUMMARY OF THE INVENTION

The present invention provides an open cell foam that incorporates antimicrobial properties.

The present invention provides for a foam that incorporates nanoparticles of silver into the open cell foam matrix.

The present invention provides that the foam may be made from any number of different materials including, but not limited to polyether polyurethane, polyester polyurethane, polycarbonate, thermoplastic olefin ("TPO"), thermoplastic elastomers ("TPE"), and thermoplastic polyurethanes ("TPU").

In several contemplated embodiments, the present invention provides that the nanoparticles of silver may have an average diameter of between about 10 and 30 nanometers (nm). Alternatively, the silver nanoparticles may be added to the foam with a size of between about 5-100 nanometers, with the smaller sizes being preferred to the larger sizes. In still another contemplated embodiment, the present invention may incorporate silver nanoparticles with a size of between about 5-30 nanometers. Alternatively, the present invention may include silver nanoparticles with sizes between about 10 and 30 nanometers. The present invention relies, in one contemplated specific embodiment, on silver nanoparticles with an average size of about 10 nanometers. The present invention, however, is not limited solely to silver nanoparticles of about 10 nanometers in size, but is intended to encompass a broader range of particle sizes.

With respect to the present invention, it is contemplated that the silver nanoparticles may be present in the foam matrix in a concentration presenting an area-to-volume ratio of greater than about 50,000 and less than about 400,000. In another embodiment, the area-to-volume ratio may be greater than about 100,000. In still another embodiment, the area-to-volume ratio may be greater than about 150,000. Further, it is contemplated that the silver nanoparticles may be added such that the area-to-volume ratio is greater than about 200,000. Additionally, one contemplated embodiment of the present invention may include sliver nanoparticles with an area-to-volume ratio greater than about 250,000. Another embodiment contemplates silver nanoparticles being added with an area-to-volume ratio of greater than about 300,000. Next, it is contemplated that the area-to-volume ratio for the silver nanoparticles may be about 350,000. The maximum area-to-volume ratio is believed to be about 400,000, but this is not intended to be limiting of the invention.

It is contemplated that the foam of the present invention may be reticulated via one or both of thermal and/or chemical reticulation.

The present invention also contemplates a method of manufacturing an antimicrobial foam. The method includes combining components to form a foam defining a foam matrix, mixing silver nanoparticles into the components, after mixing, curing the components with the silver nanoparticles to form the foam matrix, thereby suspending silver nanoparticles within the foam matrix, and reticulating the foam matrix to form an open-cell foam, wherein the foam matrix defines a plurality of interconnected bubbles therein.

Other aspects of the present invention will be made apparent from the discussion that follows.

BRIEF DESCRIPTION OF THE DRAWINGS

The present invention will now be described in connection with the drawings appended hereto, in which.

DETAILED DESCRIPTION OF EMBODIMENT(S) OF THE INVENTION

Figure 1:
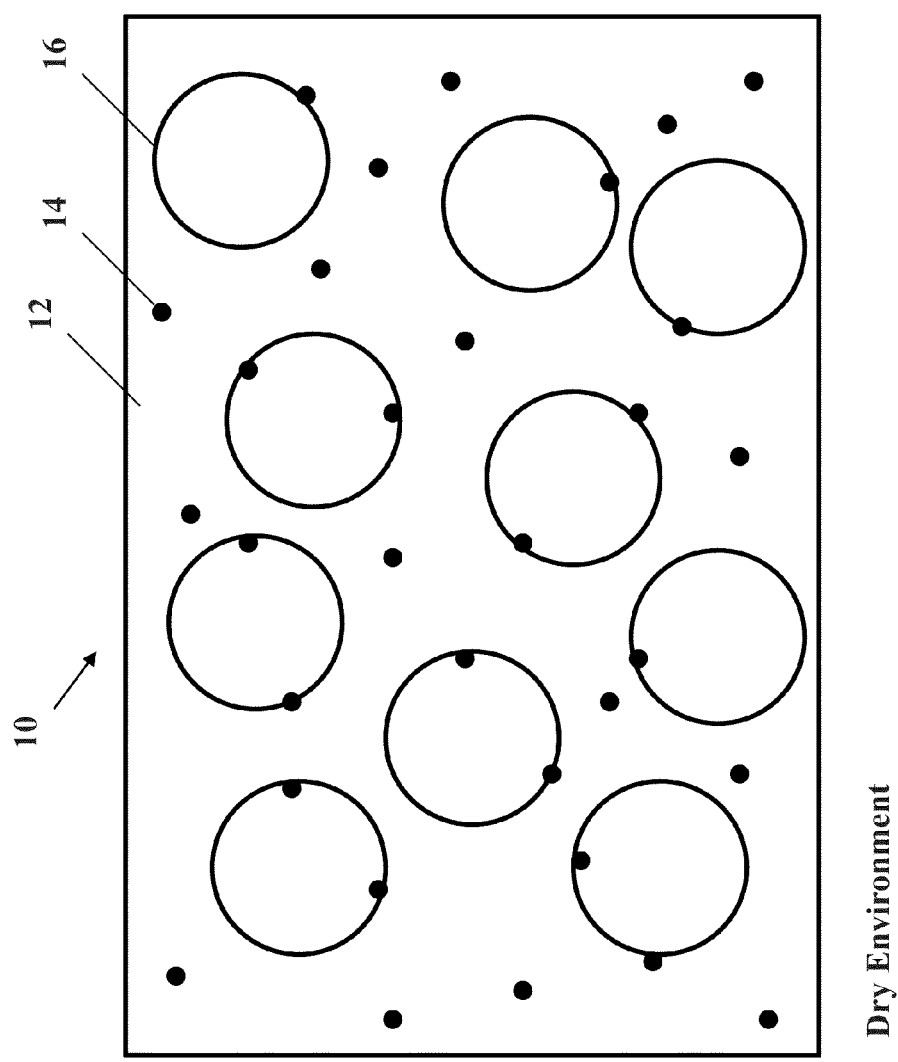
FIG. 1 is a representational schematic view of the foam according to the present invention.

The present invention will now be described with reference to one or more embodiments. The invention, however, is not intended to be limited to the embodiment(s) discussed. To the contrary, as should be apparent to those skilled in the art, there are numerous variations and equivalents that may be employed without departing from the scope and spirit of the present invention. Those equivalents and variations are intended to be encompassed by the present invention.

The present invention capitalizes, in part, on the incorporation of silver nanoparticles in foam, the details of which are provided below. In summary, the present invention incorporates silver, as an antimicrobial agent, in an open cell foam structure. The silver is embedded mixed into the foam matrix before the foam sets. As a result, the silver nanoparticles cannot be washed out of the foam during use.

As a preliminary matter, the term "antimicrobial," as used herein is intended to have its ordinary and usual meaning. So that the discussion that follows is clear, the term is intended to encompass agents that present toxicity to bacteria, fungi, viruses, and other microorganisms.

Before delving into specific characteristics, the present invention is an open cell foam into which nanoparticles of silver are dispersed. It is believed that the silver nanoparticles, when exposed to water (i.e., in an aqueous environment), deliver silver ions into the environment. In other words, moisture activates the silver nanoparticles suspended in the foam. The silver ions, which are most likely Ag+ ions, bind to organic proteins, thereby deactivating the microorganism, such as bacteria, fungi, viruses, etc. It is noted that, while Ag+ ions are referred to herein, it is possible that other silver ions may be generated. As a result, reference to Ag+ ions are intended to encompass other ions as well.

The foam of the present invention may be either a closed cell or an open cell foam. An open cell foam is preferred because the open cell structure presents a greater surface area to the internal matrix. As a result, there is a greater opportunity for the silver nanoparticles to be exposed to the aqueous environment.

The foam may be made from any number of different materials including, but not limited to polyether polyurethane, polyester polyurethane, polycarbonate, thermoplastic olefin ("TPO"), thermoplastic elastomers ("TPE"), and thermoplastic polyurethanes ("TPU").

While not intended to be limiting of the material, the term thermoplastic olefins is understood to refer to polymer/filler blends usually including some fraction of polypropylene ("PP"), polyethylene ("PE"), block copolymer polypropylene ("BCPP"), rubber, and a reinforcing filler. Common fillers include, but are not restricted to, talc, fiberglass, carbon fiber, wollastonite, and metal oxy sulfates ("MOS"). Common rubbers include, but are not limited to ethylene-propylene rubber ("EPR"), ethylene-propylene-diene rubber ("EPDM"), ethylene-octene rubber ("EOR"), ethylene-butadiene rubber ("EBR"), and styrene-ethylene-butadiene-styrene rubber (SEBSR")

Thermoplastic elastomers ("TPE") are sometimes referred to as thermoplastic rubbers. Thermoplastic elastomers encompass a wide range of materials that include, but are not limited to a class of copolymers or a physical mix of polymers (usually a plastic and a rubber) which consist of materials with both thermoplastic and elastomeric properties. While most elastomers are thermosets, thermoplastics are relatively easy to use in manufacturing, for example, by injection molding. Thermoplastic elastomers show both advantages typical of rubbery materials and plastic materials. A difference between thermoset elastomers and thermoplastic elastomers is the type of crosslinking bond in their structures. Crosslinking is one structural factor which contributes to highly elastic properties. The crosslinking in thermoset polymers is typically via a covalent bond created during the vulcanization process. On the other hand the crosslinking in thermoplastic elastomer polymers typically is a weaker, dipole bond, hydrogen bond, or takes place in one of the phases of the material. Among the many classes of TPEs, there are six classes that are recognized commercially. They are styrenic block copolymers, polyolefin blends, elastomeric alloys (TPE-v or TPV), thermoplastic polyurethanes, thermoplastic copolyesters, and thermoplastic polyamides.

Thermoplastic polyurethanes ("TPU") are a class of plastics with many useful properties, including elasticity, transparency, and resistance to oil, grease and resistance to abrasion, among others. TPUs are thermoplastic elastomers consisting of linear segmented block copolymers composed of hard and soft segments. TPUs may be formed by the reaction of: (1) diisocyanates with short-chain diols (so-called chain extenders) and (2) diisocyanates with long-chain bifunctional diols (known as polyols). There are virtually an unlimited amount of possible combinations which makes the variety of different TPUs enormous. TPUs may be clear and stretchy substances.

While the present invention specifically focuses on antimicrobial foams, it is noted that the present invention also may be applied to coatings, adhesives, sealants, and other elastomers. Accordingly, the present invention is not intended to be limited solely to the context of foams.

The silver nanoparticles are added to the foam have a size of between about 5-100 nanometers, with the smaller sizes being preferred to the larger sizes. More specifically, the present invention incorporates silver nanoparticles with a size of between about 5-30 nanometers. Alternatively, the present invention encompasses silver nanoparticles with sizes between about 10 and 30 nanometers. The present invention relies on silver nanoparticles with an average size of about 10 nanometers, as a general rule. Of course, as indicated above, the present invention is not limited solely to silver nanoparticles of about 10 nanometers in size, but encompasses a broader range.

Reference is now made to FIG. 1, which provides a general schematic view of the construction of one contemplated embodiment of the present invention. As illustrated, FIG. 1 shows the antimicrobial foam 10 of the present invention including a foam matrix 12 with a plurality of silver nanoparticles 14 suspended in the foam matrix 12. The foam matrix 12 also includes a plurality of bubbles 16.

In FIG. 1, the bubbles 16 are shown as independent from one another. This would suggest a closed cell foam. However, this illustration is intended to by representative of the invention. As discussed above, the antimicrobial foam 10 is contemplated to be an open cell foam, since the open cell structure provides a greater surface area for the matrix 12 and, therefore, presents a larger amount of silver nanoparticles 14 for activation in an aqueous environment.

It is noted that the antimicrobial foam 10 in FIG. 1 is illustrated in a dry environment. Accordingly, the nanosilver particles 14 have not been activated by moisture so as to generate silver ions in solution.

Figure 2:
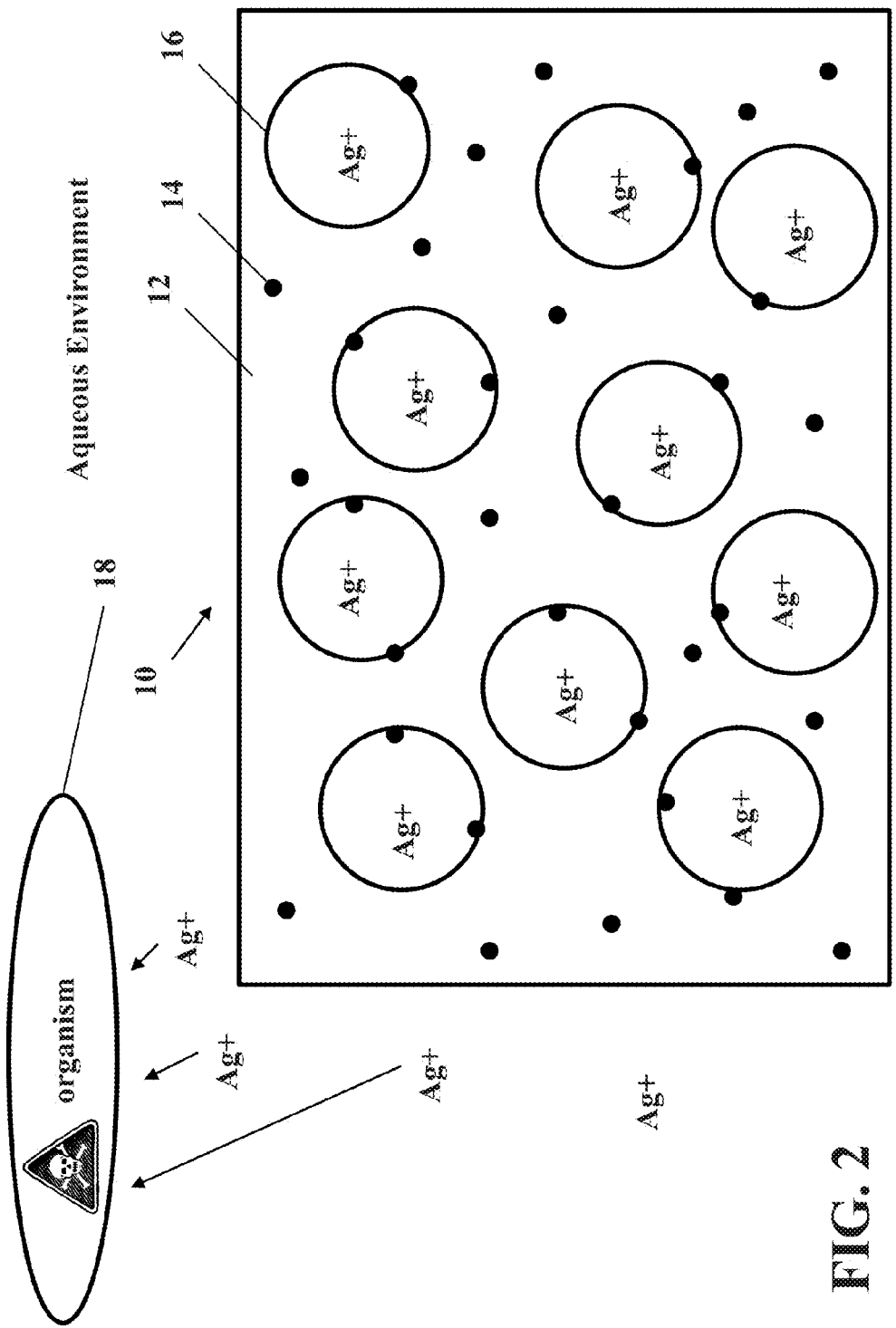
FIG. 2 is a representational schematic view of the foam according to the present invention, illustrating the dispersion of silver ions when the foam is immersed in and/or exposed to an aqueous solution.

FIG. 2 provides a schematic illustration of the antimicrobial foam 10 of the present invention in an aqueous environment, where a plurality of silver ions (Ag+) are dissolved in the solution. FIG. 2 also provides a schematic representation of an organism 18, such as a bacterium, that is adjacent to the antimicrobial foam 10. The silver ions Ag+ in solution interact with the organism 18, which has a toxic effect on the organism 18, as discussed above. It is noted that the organism 18 may be any one of a number of organisms in solution. Such organisms include, but are not limited to bacteria, fungi, and viruses.

For purposes of the present invention, it is assumed that the silver nanoparticles 14 are effectively spherical in shape. While this assumption is not meant to convey that the silver nanoparticles are, in fact, spherical, this assumption assists with a discussion of FIG. 3.

Figure 3:
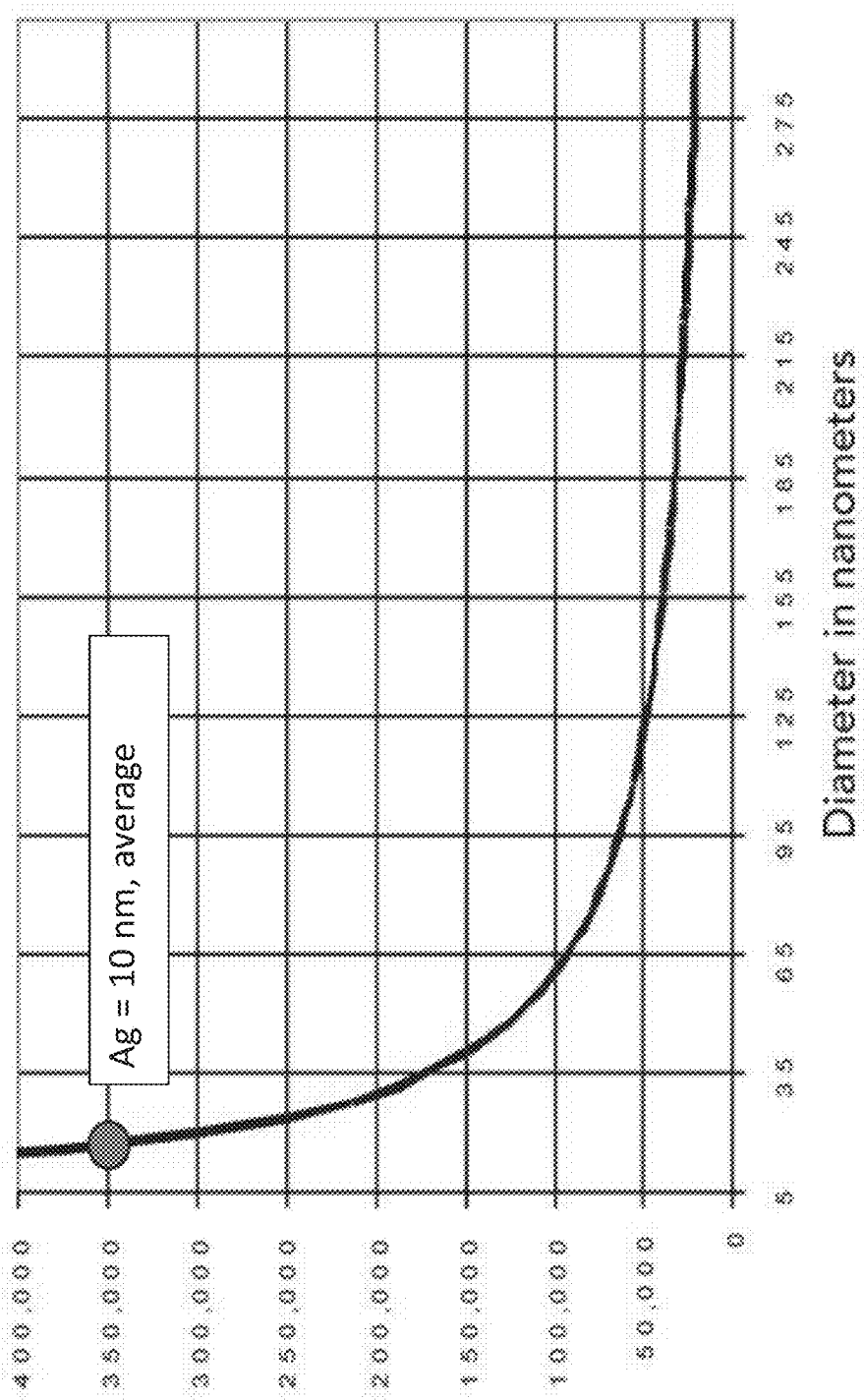
FIG. 3 is a graph illustrating the relationship between the size of a silver nanoparticle and the surface area that the nanoparticle presents.

FIG. 3 is a graph that illustrates the how the diameter of the silver nanoparticles 14 affects the surface area of the silver nanoparticles 14. It is noted that the surface area of a sphere is given by the following equation:

$$A = 4 \cdot \pi \cdot r^2 \quad (1).$$

Accordingly, the surface area, A, of a sphere is proportional to the square of the radius of the sphere. The volume of a sphere is defined by the following equation:

$$V = 4/3 \cdot \pi \cdot r^3 \quad (2).$$

Accordingly, the volume of a sphere is proportional to the cube of the radius of the sphere. From these equations, then, a ratio of the area to the volume of a spherical body, A/V, is proportional to the inverse of the radius of the sphere (1/r). In other words, as the radius of the sphere becomes smaller, the area to volume ratio increases.

The inventors of the antimicrobial foam 10 of the present invention recognized the importance of this ratio when developing the antimicrobial foam 10 of the present invention. As illustrated in FIG. 3, the smaller the diameter of the silver nanoparticles 14, the greater the effective surface area presented by those particles as a whole. It is estimated, for example, that nanosilver particles 14 with a diameter of about 10 nanometers present between 7 and 8 times more surface area than an equal volume of particles that are 100 nanometers in diameter.

For purposes of the present invention, it is contemplated that the silver nanoparticles 14 will be present in the foam matrix 12 in a concentration presenting an area-to-volume ratio of greater than about 50,000 and less than about 400,000. In another embodiment, the area-to-volume ratio is greater than 100,000. In still another embodiment, the area-to-volume ratio is greater than about 150,000. Further, it is contemplated that the silver nanoparticles 14 will be added such that the area-to-volume ratio is greater than about 200,000. Additionally, one embodiment of the present invention includes sliver nanoparticles with an area-to-volume ratio greater than about 250,000. Another embodiment contemplates silver nanoparticles 14 being added with an area-to-volume ratio of greater than about 300,000. Next, it is contemplated that the area-to-volume ratio for the silver nanoparticles 14 will be about 350,000. As noted, the maximum area-to-volume ratio is believed to be about 400,000.

As may also be apparent to those skilled in the art, the ability of a material to release ions into solution is dependent upon the surface area that the material presents to the solution. In other words, the greater the surface area presented by the material to the solution, the larger the amount of ions that are likely to be released into the solution. In the context of the present invention, therefore, the greater the surface area of the silver nanoparticles 14, the greater the ability of the silver nanoparticles 14 to release silver ions Ag+ into the solution.

From the foregoing, therefore, there is a distinct advantage to silver nanoparticles 14 with a small size. The smaller the silver nanoparticles 14, the greater the probability (and, therefore, the greater the concentration) of silver ions Ag+ in the solution. There is a further advantage of small silver nanoparticles 14. When the silver nanoparticles 14 have small diameters, a smaller volume of silver needs to be added to the foam matrix 12 to provide efficacious antimicrobial properties to the antimicrobial foam 10. Since silver is a relatively expensive material, reducing the amount of silver added has advantages with respect to cost. In addition, when the silver nanoparticles 14 are small, they are not expected to have an adverse effect on the formation of the foam matrix 12 due to their small size.

While not apparent from FIG. 1 or 2, the silver nanoparticles 14 have a size that is significantly smaller than the associated bubbles 16 in the foam matrix 12. It is believed that the bubbles 16 will be approximately 1000 times larger in size than the silver nanoparticles 14.

Figure 6:
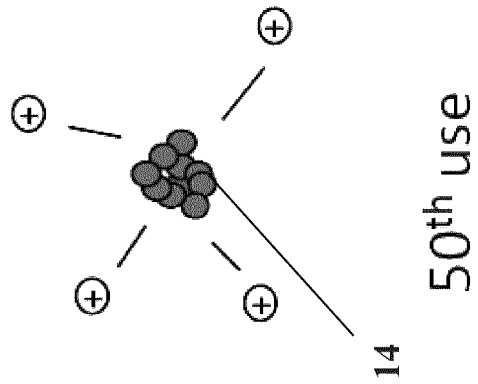
FIGS. 4-6 illustrate the gradual dissolution of silver nanoparticles over a period of time.
Figure 5:
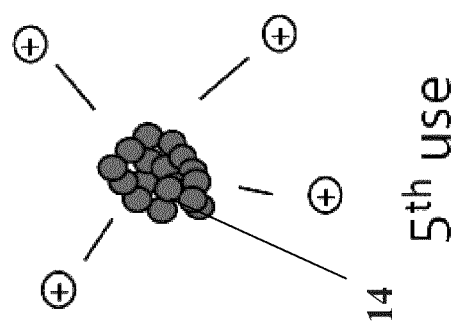
Figure 4:
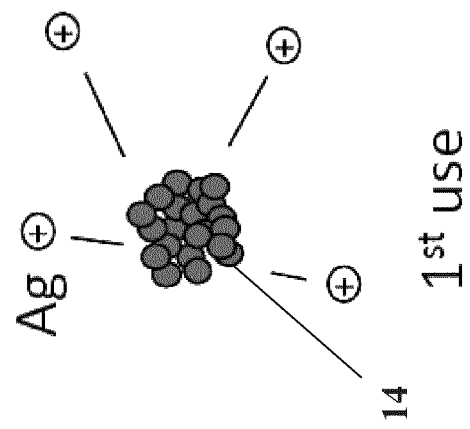

Reference is now made to FIGS. 4-6, which provides three illustrations of the progressive dissolution of a typical silver nanoparticle 14 suspended in the foam matrix 12. FIG. 4 provides a representative illustration of the initial size of the silver nanoparticle 14 at the first use of the antimicrobial foam 10 of the present invention. Once exposed to an aqueous environment, the silver nanoparticle 14 is expected to release one or more silver ions Ag+ into solution. As a result, the size of the silver nanoparticle 14 will be slightly diminished. Continued and/or repetitive use will cause further silver ions Ag+ to be released. As such, FIG. 5 provides an illustration of the silver nanoparticle 14 after the fifth use. FIG. 6 illustrates the silver particle 14 after the fiftieth use. As may be apparent, continuous and/or repetitive use further depletes the availability of the silver in the antimicrobial foam 10.

As should be appreciated, silver nanoparticles 14, even when they are 10-30 nanometers in size, will contain a large number of silver atoms. As a result, it is anticipated that the antimicrobial foam 10 of the present invention will retain its antimicrobial properties after many repeated uses. This differs from much of the prior art where the silver is coated onto or incorporated into a substrate and, therefore, loses its efficacy after its first use (or first few uses).

Zeolites are microporous, aluminosilicate materials that are commonly used as absorbents, because zeolites have a high affinity for capturing and retaining water. In some embodiments in the prior art, zeolites are employed as silver "sponges." In other words, zeolites impregnated with silver are added to the substrate.

Zeolites typically are much larger than the silver nanoparticles 14 of the present invention. For example, zeolite particles may be on the order of 1.5 microns (micrometers) or larger in diameter. As a result, zeolite particles are 100 to 2000 times larger than the nanosilver particles 14 of the present invention.

Figure 7:
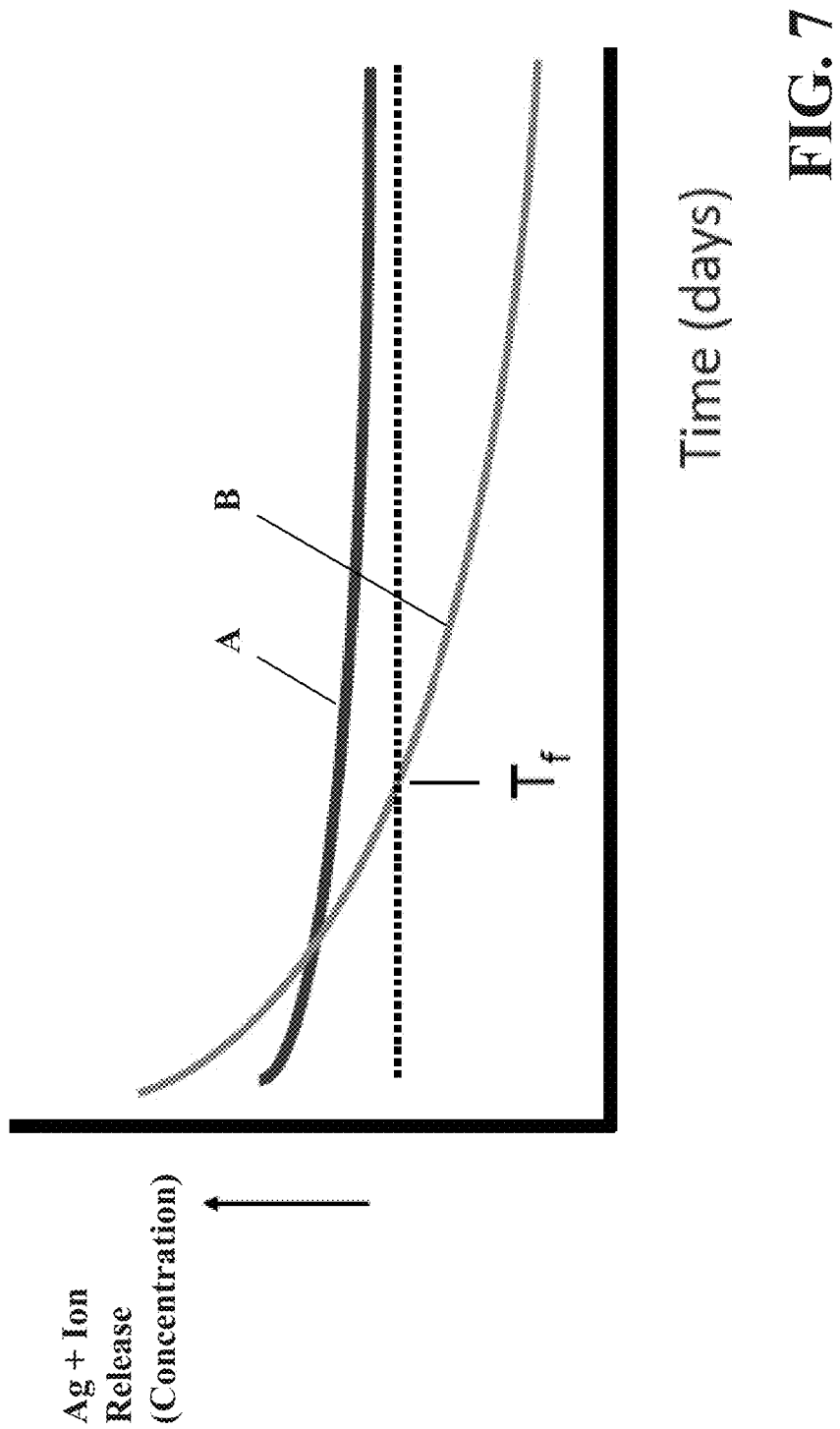
FIG. 7 is a graph illustrating the improved antimicrobial activity of the antimicrobial foam of the present invention as compared with an antibacterial foam incorporating zeolite particles.

Zeolite particles present at least two challenges to the creation of an antimicrobial foam. First, the particles are "large," and, therefore, can interfere in the formation of the foam matrix. Second, zeolites have a tendency to release their active ingredients relatively quickly. As a result, where zeolites are used in combination with silver, the effective "lifetime" of the foam will be less than the effective lifetime as compared with the antimicrobial foam 10, where zeolites are not employed in the preferred embodiment. Curve A in FIG. 7 illustrates the effective lifetime of the antimicrobial foam 10 according to the present invention. Curve B in FIG. 7 illustrates the effective lifetime of a foam that incorporates zeolite materials. As is evident, the time to failure (or loss of efficacy), $T_f$, is considerably shorter for Curve B than for Curve A, which does not show a time to failure.

While one contemplated embodiment of the antimicrobial foam 10 of the present invention contemplates the absence of zeolites (or substantially the absence of zeolites), the present invention does permit the addition of zeolites. In other words, zeolites may be present without departing from the present invention.

With respect to the foam matrix 12, the foam may be made from polyurethane, polyether, polycarbonate, or polyester, among other materials, as discussed herein. For two embodiments of the present invention, the foam is contemplated to be either a reticulated polyether or a reticulated polyester. While these materials are contemplated for the foam matrix 12, other materials may be employed without departing from the present invention, as indicated.

One contemplated embodiment of the present invention is provided in Example 1, below.

EXAMPLE 1

For Example 1, which is a reticulated polyether format foam, ingredients were mixed in the following ratios. The amounts of the ingredients are measured in parts per 100 parts of polyol. The ingredients are:
(1) 15 parts of Arcol UHS-150, which is a styrene/acrylonitrile grafted polyol from Bayer Material Science;
(2) 85 parts of Arcol F-3040, a 3000 molecular weight (m. wt.) ether polyol from Bayer Material Science, which was first polymerized with 3.0 parts of Mondur TD-80, a blend of 80% 2,4-toluene diisocyanate and 20% 2,6-toluene diisocyanate from Bayer Material Science,
(3) 1.0 parts of SmartSilver™, a 5.0% weight/weight nanosilver dispersion in dipropylene glycol from NanoHorizons,
(4) 1.32 parts of Superblack 1127, a carbon/polyester dispersion from Rebus, Inc.,
(5) 0.50 parts of Niax Silicone L-620, a polyalkyleneoxidemethylsiloxane and copolymer from Momentive,
(6) 0.14 parts of Kosmos 10P, a 33% solution of stannous octoate in mineral oil from Degussa,
(7) 0.33 parts of Dabco 33-LV, a 33% solution of triethylenediamine in dipropylene glycol from Air Products,
(8) 4.85 parts of deionized water, and
(9) 57.6 parts of Mondur TD-80, a blend of 80% 2,4-toluene diisocyanate and 20% 2,6-toluene diisocyanate from Bayer Material Science.

The resulting foam was thermally reticulated to an open cell foam and had the following properties: (1) a density of 1.31 pounds per cubic foot (pcf), (2) an air flow of 12.0 cubic feet per minute (cfm), and (3) a 25% CFD of 0.54 pounds per square inch (psi) according to ASTM Testing Standard D 3574-05. It is noted that the term "CFD" refers to Compression Force Deflection, which should be understood by those skilled in the art. 25% CFD refers to a test where the foam is compressed to 25% of its thickness before the force is measured.

The foam produced according to Example 1 was tested according to antimicrobial activity according to ASTM E 2149-01 using *Escherichia Coli* (*E. Coli*) with 1.0 g of the foam in 25 ml of innoculum. After twenty-four (24) hours, the initial concentration (measured in CFU/ml="colony forming units" per milliliter) of $2.75 \times 10^5$ was reduced to $1.03 \times 10^2$. This demonstrates a 99.9% reduction in microbial activity, as should be appreciated by those skilled in the art.

EXAMPLE 2

In a second example, a reticulated ester foam was produced in a manner similar to that described in Example 1. Here, 1.0 parts of SmartSilver™ was mixed with the components of the foam. The foam was reticulated, as in Example 1. The foam also was tested for antimicrobial activity according to AATCC™ 100-2004 using *Escherichia Coli* (*E. Coli*) with 1.0 g of the foam in 25 ml of innoculum. After twenty-four (24) hours, there was a 99.5% reduction in microbial activity.

As identified in Examples 1 and 2 above, it is contemplated that the silver nanoparticles 14 will be introduced into the foam matrix 12 via a slurry of 5% silver nanoparticles suspended in PDG (dipropylene glycol). The silver nanoparticles 14 may be introduced in any number of alternative ways without departing from the scope of the present invention.

Given the large surface area of the silver nanoparticles 14, as discussed above, it is contemplated that only 0.032% by weight of silver nanoparticles 14 are required in the foam matrix 12. Within the context of the present invention, it is contemplated that the silver nanoparticles 14 may be incorporated into the foam matrix 12 in a concentration of up to 0.20 weight-%. In one embodiment, the silver nanoparticles 14 will be incorporated in an amount of 0.15 weight-% or less. In another contemplated embodiment, the silver nanoparticles 14 are incorporated into the foam matrix 12 in a concentration of 0.10 weight-% or less. In still another embodiment, the concentration of silver nanoparticles 14 is 0.05 weight-% or less. It is also contemplated that the silver nanoparticles 14 are incorporated into the foam matrix 12 in an amount greater than 0.01 weight-%.

With respect to the manufacture of the antimicrobial foam 10 according to the present invention, the various ingredients for the foam matrix 12 and the silver nanoparticles 14 were combined on a laboratory scale by mixing together the ingredients identified in Example 1 and pouring them into a 9×9 inch open mold. The foam matrix 12 was allowed to free rise under atmospheric pressure (e.g., 1 atm) and temperature (about 72° F.). The foam was then cured at ambient temperatures overnight before being thermally reticulated with an explosive mixture of hydrogen and oxygen.

It is noted that the antimicrobial foam 10 of the present invention need not be thermally reticulated. It is contemplated that the antimicrobial foam 10 may be chemically reticulated. Other methods of reticulation also may be employed without departing from the scope of the present invention.

As should be appreciated by those skilled in the art, other methods of manufacture may be employed without departing from the scope of the present invention.

As noted above, the present invention is not limited solely to the embodiments described above. The present invention is intended to encompass equivalents and variations that would be apparent to those skilled in the art.

What is claimed is:
1. An antimicrobial foam, comprising:
an open-cell foam in a foam matrix defining a plurality of interconnected bubbles therein;
silver nanoparticles; and
zeolites, into which the silver nanoparticles are impregnated, suspended within the foam matrix,
wherein the foam matrix comprises at least one material selected from a group comprising polyether polyure- thane, polyester polyurethane, polycarbonate, thermoplastic olefin, thermoplastic elastomer, and thermoplastic polyurethane, wherein the silver nanoparticles have an average size between about 5 and less than 30 nanometers, and wherein the silver nanoparticles are incorporated into the foam matrix in a concentration of between about 0.01 weight-% and about 0.05 weight-%.

2. The antimicrobial foam of claim 1, wherein the zeolites are 100 to 2000 times larger than the silver nanoparticles.

3. The antimicrobial foam of claim 2, wherein the zeolites have a diameter of about 1.5 microns.

4. The antimicrobial foam of claim 1, wherein the silver nanoparticles have an average size between about 10 and less than 30 nanometers.

5. The antimicrobial foam of claim 1, wherein the silver nanoparticles have a concentration of about 0.032 weight-%.

6. The antimicrobial foam of claim 1, wherein the foam matrix is a reticulated foam.

7. The antimicrobial foam of claim 6, wherein the foam is reticulated via at least one selected from a group comprising thermal and chemical reticulation.

8. The antimicrobial foam of claim 1, wherein the thermoplastic olefin comprises at least one of polypropylene, polyethylene, block copolymer polypropylene, and rubber.

9. The antimicrobial foam of claim 8, further comprising a filler in the thermoplastic olefin, wherein the filler comprises at least one of talc, fiberglass, carbon fiber, wollastonite, and metal oxy sulfates.

10. The antimicrobial foam of claim 8, wherein the rubber comprises at least one of ethylene-propylene rubber, ethylene-propylene-diene rubber, ethylene-octene rubber, ethylene-butadiene rubber, and styrene-ethylene-butadiene-styrene rubber.

11. The antimicrobial foam of claim 1, wherein the thermoplastic elastomer comprises at least one of styrene block copolymers, polyolefin blends, elastomeric alloys, thermoplastic polyurethanes, thermoplastic copolyesters, and thermoplastic polyamides.

12. The antimicrobial foam of claim 1, wherein the thermoplastic polyurethane result from a reaction between at least one of (1) diisocyanates with short-chain diols and (2) diisocyanates with long-chain bifunctional diols.

13. The antimicrobial foam of claim 1, wherein the bubbles are about 1000 times larger than the silver nanoparticles.

14. An antimicrobial foam, comprising:
an open-cell foam in a foam matrix defining a plurality of interconnected bubbles therein; and
silver nanoparticles suspended within the foam matrix,
wherein the silver nanoparticles have an average size between about 5 and 100 nanometers,
wherein the silver nanoparticles are incorporated into the foam matrix in a concentration of between about 0.01 weight-% and about 0.20 weight-%; and
wherein the foam matrix is a reticulated polyether foam comprising:
15 parts of a styrene/acrylonitrile grafted polyol;
85 parts of a 3000 molecular weight ether polyol, which is first polymerized with 3.0 parts of a blend of 80% 2,4-toluene diisocyanate and 20% 2,6-toluene diisocyanate;
1.0 parts of a 5.0% weight/weight nano-silver dispersion in dipropylene glycol;
1.32 parts of a carbon/polyester dispersion;
0.50 parts of a polyalkyleneoxidemethylsiloxane and copolymer;
0.14 parts of a 33% solution of stannous octoate in mineral oil;
0.33 parts of a 33% solution of triethylenediamine in dipropylene glycol;
4.85 parts of deionized water; and
57.6 parts of a blend of 80% 2,4-toluene diisocyanate and 20% 2,6-toluene diisocyanate.

15. A method of manufacturing an antimicrobial foam, comprising:
combining components to form a foam defining a foam matrix;
mixing zeolites impregnated with silver nanoparticles into the components;
after mixing, curing the components with the zeolites impregnated with silver nanoparticles to form the foam matrix, thereby suspending zeolites impregnated with silver nanoparticles within the foam matrix; and
reticulating the foam matrix to form an open-cell foam, wherein the foam matrix defines a plurality of interconnected bubbles therein;
wherein the foam matrix comprises at least one material selected from a group comprising polyether polyurethane, polyester polyurethane, polycarbonate, thermoplastic olefin, thermoplastic elastomer, and thermoplastic polyurethane,
wherein the silver nanoparticles have an average size between about 5 and less than 30 nanometers, and
wherein the silver nanoparticles are incorporated into the foam matrix in a concentration of between about 0.01 weight-% and about 0.05 weight-%.

16. The method of claim 15, wherein reticulating is accomplished via at least one selected from a group comprising thermal and chemical reticulation.

17. The method of claim 15, wherein the components comprise:
15 parts of a styrene/acrylonitrile grafted polyol;
85 parts of a 3000 molecular weight ether polyol, which is first polymerized with 3.0 parts of a blend of 80% 2,4-toluene diisocyanate and 20% 2,6-toluene diisocyanate;
1.0 parts of a 5.0% weight/weight nano-silver dispersion in dipropylene glycol;
1.32 parts of a carbon/polyester dispersion;
0.50 parts of a polyalkyleneoxidemethylsiloxane and copolymer;
0.14 parts of a 33% solution of stannous octoate in mineral oil;
0.33 parts of a 33% solution of triethylenediamine in dipropylene glycol;
4.85 parts of deionized water; and
57.6 parts of a blend of 80% 2,4-toluene diisocyanate and 20% 2,6-toluene diisocyanate.

* * * * *